United States Patent
Druke et al.

(10) Patent No.: US 11,717,683 B2
(45) Date of Patent: Aug. 8, 2023

(54) NON-INVASIVE NERVE STIMULATION

(71) Applicant: Neurostim OAB, Inc., Waltham, MA (US)

(72) Inventors: Michael Bernard Druke, Half Moon Bay, CA (US); Alan E. Loh, Los Altos, CA (US); Robert W. Scott, El Granada, CA (US); Anthony Wei, Palo Alto, CA (US); Graham Harold Creasey, Menlo Park, CA (US); Hoo-Min D. Toong, Cambridge, MA (US)

(73) Assignee: Neurostim OAB, Inc.

( * ) Notice: Subject to any disclaimer, the term of this patent is extended or adjusted under 35 U.S.C. 154(b) by 393 days.

(21) Appl. No.: 17/030,686

(22) Filed: Sep. 24, 2020

(65) Prior Publication Data

US 2021/0016088 A1    Jan. 21, 2021

Related U.S. Application Data

(63) Continuation of application No. 15/882,213, filed on Jan. 29, 2018, now abandoned.

(60) Provisional application No. 62/582,634, filed on Nov. 7, 2017.

(51) Int. Cl.
*A61N 1/36* (2006.01)
*A61N 1/08* (2006.01)

(52) U.S. Cl.
CPC .......... *A61N 1/36014* (2013.01); *A61N 1/08* (2013.01); *A61N 1/3603* (2017.08)

(58) Field of Classification Search
CPC . A61N 1/36014; A61N 1/0456; A61N 1/0476
See application file for complete search history.

(56) References Cited

U.S. PATENT DOCUMENTS

| | | |
|---|---|---|
| 5,433,737 A | 7/1995 | Aimone |
| 6,081,744 A | 6/2000 | Loos |
| 6,155,976 A | 12/2000 | Sackner et al. |
| 6,819,956 B2 | 11/2004 | DiLorenzo |
| 7,616,988 B2 | 11/2009 | Stahmann et al. |

(Continued)

FOREIGN PATENT DOCUMENTS

| | | |
|---|---|---|
| CN | 101868279 A | 10/2010 |
| JP | 2010004961 A | 1/2010 |

(Continued)

OTHER PUBLICATIONS

Aksu et al.; State dependent excitability changes of spinal flexor reflex in patients with restless legs syndrome secondary to chronic renal failure; Sleep Medicine; 2002; 3(5); 427-430.

(Continued)

*Primary Examiner* — Joseph M Dietrich
(74) *Attorney, Agent, or Firm* — Potomac Law Group, PLLC

(57) ABSTRACT

One example provides a nerve stimulation treatment using electrodes coupled to a user. Examples determine a target charge level and output a series of pulses from the electrodes. For each pulse outputted, examples measure a charge value of the pulse and compare the charge value to the target charge level. If the charge value is greater than the target charge level, examples reduce a strength level of a subsequent outputted pulse. If the charge value is less than the target charge level, examples increase the strength level of a subsequent outputted pulse.

21 Claims, 11 Drawing Sheets

(56) References Cited

U.S. PATENT DOCUMENTS

| | | |
|---|---|---|
| 7,643,874 B2 | 1/2010 | Nitzan et al. |
| 7,689,285 B2 | 3/2010 | Garabet |
| 7,887,493 B2 | 2/2011 | Stahmann et al. |
| 7,922,676 B2 | 4/2011 | Daskal et al. |
| 7,974,696 B1 | 7/2011 | DiLorenzo |
| 8,386,032 B2 | 2/2013 | Bachinski et al. |
| 8,498,698 B2 | 7/2013 | Donofrio et al. |
| 8,657,756 B2 | 2/2014 | Stahmann et al. |
| 8,688,190 B2 | 4/2014 | Libbus et al. |
| 9,855,427 B2 | 1/2018 | Bennett et al. |
| 10,342,977 B2 | 7/2019 | Raghunathan |
| 10,737,096 B1 | 8/2020 | Klee |
| 2002/0019652 A1 | 2/2002 | Silva et al. |
| 2004/0049241 A1 | 3/2004 | Campos |
| 2004/0133164 A1 | 7/2004 | Funderburk et al. |
| 2006/0004424 A1 | 1/2006 | Loeb et al. |
| 2008/0027507 A1 | 1/2008 | Bijelic et al. |
| 2008/0149102 A1 | 6/2008 | Kim et al. |
| 2009/0048643 A1 | 2/2009 | Erickson et al. |
| 2009/0132018 A1 | 5/2009 | DiUbaldi et al. |
| 2009/0149912 A1 | 6/2009 | Dacey, Jr. et al. |
| 2009/0182393 A1 | 7/2009 | Bachinski |
| 2010/0204538 A1 | 8/2010 | Burnett et al. |
| 2010/0249637 A1 | 9/2010 | Walter et al. |
| 2011/0160806 A1 | 6/2011 | Lyden et al. |
| 2013/0030257 A1 | 1/2013 | Nakata et al. |
| 2013/0060149 A1 | 3/2013 | Song et al. |
| 2014/0194951 A1 | 7/2014 | Gong et al. |
| 2014/0228927 A1 | 8/2014 | Ahmad et al. |
| 2014/0324120 A1 | 10/2014 | Bogie et al. |
| 2015/0164401 A1 | 6/2015 | Toth et al. |
| 2015/0335888 A1 | 11/2015 | Demers et al. |
| 2016/0015962 A1 | 1/2016 | Maragheh et al. |
| 2016/0213922 A1 | 7/2016 | Goldberg et al. |
| 2016/0263376 A1 | 9/2016 | Yoo et al. |
| 2017/0001003 A1 | 1/2017 | Pivonka et al. |
| 2017/0215745 A1 | 8/2017 | Felix et al. |
| 2017/0224990 A1 | 8/2017 | Goldwasser et al. |
| 2017/0312512 A1 | 11/2017 | Creasey et al. |
| 2017/0312526 A1 | 11/2017 | Steinke et al. |
| 2017/0333695 A1 | 11/2017 | Kaplan et al. |
| 2018/0020951 A1 | 1/2018 | Kaifosh et al. |
| 2018/0116877 A1 | 5/2018 | Ineichen |
| 2018/0133479 A1 | 5/2018 | Bennett et al. |
| 2018/0140859 A1 | 5/2018 | Meir |
| 2018/0154147 A1 | 6/2018 | Izvorski et al. |
| 2018/0161586 A1 | 6/2018 | Beyer et al. |
| 2018/0214054 A1 | 8/2018 | Soltani et al. |
| 2018/0318585 A1 | 11/2018 | Pfeifer |
| 2018/0350451 A1 | 12/2018 | Ohnemus et al. |
| 2019/0114766 A1 | 4/2019 | Song et al. |
| 2019/0117976 A1 | 4/2019 | Belson et al. |
| 2019/0134391 A1 | 5/2019 | Druke et al. |
| 2019/0134396 A1 | 5/2019 | Toth et al. |
| 2019/0189253 A1 | 6/2019 | Kartoun et al. |
| 2019/0198144 A1 | 6/2019 | Blackley et al. |
| 2019/0282822 A1 | 9/2019 | Freeman et al. |
| 2019/0313934 A1 | 10/2019 | Lee et al. |
| 2019/0336763 A1 | 11/2019 | Spurling et al. |
| 2020/0069941 A1 | 3/2020 | Campean et al. |
| 2020/0069942 A1 | 3/2020 | Campean et al. |
| 2020/0139118 A1 | 5/2020 | John et al. |
| 2020/0338333 A1 | 10/2020 | Toong et al. |
| 2020/0338334 A1 | 10/2020 | Toong et al. |
| 2020/0376266 A1 | 12/2020 | Toong et al. |

FOREIGN PATENT DOCUMENTS

| | | |
|---|---|---|
| JP | 2011502707 A | 1/2011 |
| WO | 2009064641 A1 | 5/2009 |
| WO | 2011053607 A1 | 5/2011 |
| WO | 2014194200 A1 | 12/2014 |
| WO | 2015183620 A3 | 4/2016 |
| WO | 2017178946 A1 | 10/2017 |

OTHER PUBLICATIONS

Bucher, SF, et al.; Reflex studies and MRI in the restless legs syndrome; Acta Neurologica Scandinavica; 1996; 94(2); 145-150.

Cogiamanian et al.; Transcutaneous spinal cord direct current stimulation inhibits the lower limb nociceptive iexion reflex in human beings; Pain; 2011; 152(2); 370-375.

Dafkin, C, et al.; Circadian variation of flexor withdrawal and crossed extensor reflexes in patients with restless legs syndrome; Journal of Sleep Research; 2018; 27(5); 1-7.

Entezari-Taher, M, et al.; Changes in excitability of motor cortical circuitry in primary restless legs syndrome; Neurology; 1999; 53(6); 1201-1205.

Garrison, MK, et al.; Flexor reflex decreases during sympathetic stimulation in chronic human spinal cord injury; Experimental Neurology; 2009; 219(2); 507-515.

Gemignani, F; Restless legs syndrome from the spinal cord perspective: A flexor reflex circuitopathy?; Journal of Sleep Research; 2018; 27(5); 1-2.

Gregori; Suppression of flexor reflex by transcutaneous electrical nerve stimulation in spinal cord injured patients; Muscle and Nerve; 1998; 21(2); 166-172.

Guo, S, et al.; Restless legs syndrome: From pathophysiology to clinical diagnosis and management; Frontiers in Aging Neuroscience; 2017; 9(JUN); 1-14.

Heide, AC, et al.; Effects of transcutaneous spinal direct current stimulation in idiopathic restless legs patients; Brain Stimulation; 2014; 7(5); 636-642.

Karatas, M; Restless legs syndrome and periodic limb movements during sleep: Diagnosis and treatment; Neurologist; 2007; 13(5); 294-301.

Koo, BB, et al.; Restless Legs Syndrome: Current Concepts about Disease Pathophysiology; Tremor and other Hyperkinetic Movements; 2016; 6(0); 401.

Krueger; Restless Legs Syndrome and Periodic Movements of Sleep; Mayo Clinic Proceedings; 1990; 65(7); ?99-1006.

Merkl, et al.; Vagus nerve stimulation improves restless legs syndrome associated with major depression: A case report [3]; Journal of Clinical Psychiatry; 2007; 68 (4); 635-636.

Ninos et al.; Restless Legs Syndrome Fact Sheet Restless Legs Syndrome Fact Sheet What is restless legs syndrome; 2019; 1-8.

Patel, Kilhertz Electrical Stimulation Nerve Conduction Block: Effects of Electrode Surface Area, IEEE Transactions on Neural Systems and Rehabilitation Engineering, vol. 25, No. 10, Oct. 2017.

Ristanovi et al.; Nonpharmacologic treatment of periodic leg movements in sleep; Archives of Physical Medicine and Rehabilitation; 1991; 72(6); 385-389.

Rizzo, V, et al.; Dopamine agonists restore cortical plasticity in patients with idiopathic restless legs syndrome; Movement Disorders; 2009; 24(5); 710-715.

Roby-Brami, A, et al.; Inhibitory effects on flexor reflexes in patients with a complete spinal cord lesion; ExperimentalBrain Research; 1992; 90(1); 201-208.

Rozeman, AD, et al.; Effect of sensory stimuli on restless legs syndrome: A randomized crossover study; Journal of Clinical Sleep Medicine; 2014; 10(8); 893-896.

Sharon, D, et al.; Restless Legs Syndrome and Periodic Limb Movement Disorder in Children; Journal of Child Science; 2019; 9(1); E38-E49.

Yam, MF, et al.; General pathways of pain sensation and the major neurotransmitters involved in pain regulation; International Journal of Molecular Sciences; 2018; 19(8).

Yogi A. Patel; Kilohertz Electrical Stimulation Nerve Conduction Block: Effects of Electrode Surface Area; IEEET-ransactions on Neural Systems and Rehabilitation Engineering, vol. 25, No. 10, Oct. 2017.

NON-INVASIVE NERVE STIMULATION

CROSS REFERENCE TO RELATED APPLICATIONS

This application is a continuation of U.S. patent application Ser. No. 15/882,213, filed on Jan. 29, 2018, currently pending, which claims priority of U.S. Provisional Patent Application Ser. No. 62/582,634, filed on Nov. 7, 2017. The disclosure of each of these applications is hereby incorporated by reference.

FIELD

One example is directed generally to a nerve stimulation, and in particular to nerve stimulation using electrical signals with computer control.

BACKGROUND INFORMATION

Mammalian and human nerves control organs and muscles. Artificially stimulating the nerves elicit desired organ and muscle responses. Accessing the nerves to selectively control these responses from outside the body, without invasive implants or needles penetrating the dermis, muscle or fat tissue, is desired.

DETAILED DESCRIPTION

Figure 1:
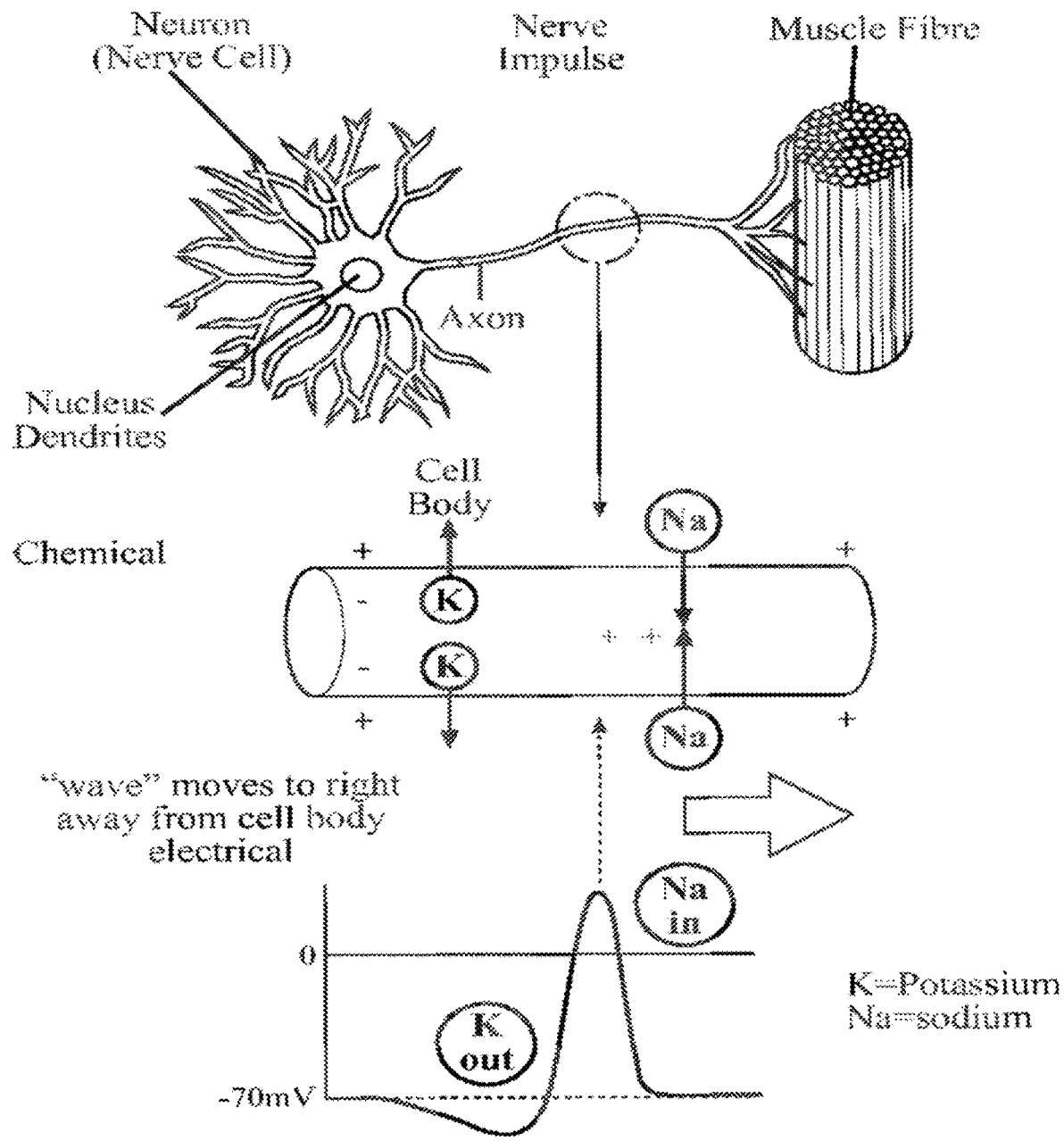
FIG. 1 is a depiction of a neuron activating a muscle by electrical impulse.

One example is a non-invasive nerve stimulator that uses feedback to adapt the nerve stimulation output. One example is implemented using a Topical Nerve Stimulator and Sensor ("TNSS") device such as disclosed in U.S. patent application Ser. No. 14/893,946, hereby incorporated by reference, and that is used to stimulate nerves. A TNSS may apply electrode-generated electric field(s) in a low frequency to dermis in the proximity of a nerve, and typically applies such a field in the magnitude of up to 100s of hertz ("Hz"). The TNSS also includes hardware and logic for high frequency ("GHz") communication to mobile devices.

A wireless system including a TNSS device is disclosed herein. Its components, features and performance characteristics are set forth in the following technical description. Advantages of a wireless TNSS system over existing transcutaneous electrical nerve stimulation devices include: (1) fine control of all stimulation parameters from a remote device such as a smartphone, either directly by the user or by stored programs; (2) multiple electrodes of a TNSS can form an array to shape an electric field in the tissues; (3) multiple TNSS devices can form an array to shape an electric field in the tissues; (4) multiple TNSS devices can stimulate multiple structures, coordinated by a smartphone; (5) selective stimulation of nerves and other structures at different locations and depths in a volume of tissue; (6) mechanical, acoustic or optical stimulation in addition to electrical stimulation; (7) the transmitting antenna of TNSS device can focus a beam of electromagnetic energy within tissues in short bursts to activate nerves directly without implanted devices; (8) inclusion of multiple sensors of multiple modalities, including but not limited to position, orientation, force, distance, acceleration, pressure, temperature, voltage, light and other electromagnetic radiation, sound, ions or chemical compounds, making it possible to sense electrical activities of muscles (EMG, EKG), mechanical effects of muscle contraction, chemical composition of body fluids, location or dimensions or shape of an organ or tissue by transmission and receiving of ultrasound.

Further advantages of the wireless TNSS system include: (1) TNSS devices are expected to have service lifetimes of days to weeks and their disposability places less demand on power sources and battery requirements; (2) the combination of stimulation with feedback from artificial or natural sensors for closed loop control of muscle contraction and force, position or orientation of parts of the body, pressure within organs, and concentrations of ions and chemical compounds in the tissues; (3) multiple TNSS devices can form a network with each other, with remote controllers, with other devices, with the Internet and with other users; (4) a collection of large amounts of data from one or many TNSS devices and one or many users regarding sensing and stimulation, collected and stored locally or through the internet; (5) analysis of large amounts of data to detect patterns of sensing and stimulation, apply machine learning, and improve algorithms and functions; (6) creation of databases and knowledge bases of value; (7) convenience, including the absence of wires to become entangled in clothing, shower proof and sweat proof, low profile, flexible, camouflaged or skin colored, (8) integrated power, communications, sensing and stimulating inexpensive disposable TNSS, consumable electronics; (9) power management that utilizes both hardware and software functions will be critical to the convenience factor and widespread deployment of TNSS device.

Referring to FIG. 1, a nerve cell normally has a voltage across the cell membrane of 70 millivolts with the interior of the cell at a negative voltage with respect to the exterior of the cell. This is known as the resting potential and it is normally maintained by metabolic reactions which maintain different concentrations of electrical ions in the inside of the cell compared to the outside. Ions can be actively "pumped" across the cell membrane through ion channels in the membrane that are selective for different types of ion, such as sodium and potassium. The channels are voltage sensitive and can be opened or closed depending on the voltage across the membrane. An electric field produced within the tissues by a stimulator can change the normal resting voltage across the membrane, either increasing or decreasing the voltage from its resting voltage.

Figure 2:
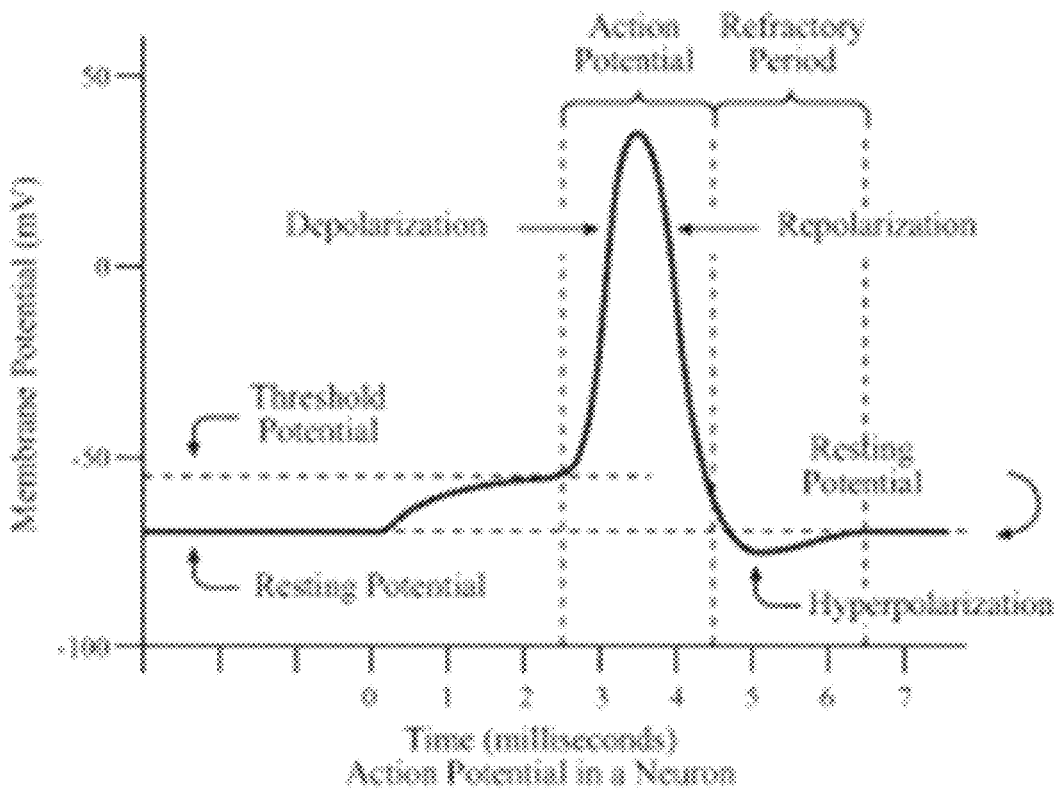
FIG. 2 is a representation of the electrical potential activation time of an electrical impulse in a nerve.

Referring to FIG. 2, a decrease in voltage across the cell membrane to about 55 millivolts opens certain ion channels, allowing ions to flow through the membrane in a self-catalyzing but self-limited process which results in a transient decrease of the trans membrane potential to zero, and even positive, known as depolarization followed by a rapid restoration of the resting potential as a result of active pumping of ions across the membrane to restore the resting situation which is known as repolarization. This transient change of voltage is known as an action potential and it typically spreads over the entire surface of the cell. If the shape of the cell is such that it has a long extension known as an axon, the action potential spreads along the length of the axon. Axons that have insulating myelin sheaths propagate action potentials at much higher speeds than those axons without myelin sheaths or with damaged myelin sheaths.

If the action potential reaches a junction, known as a synapse, with another nerve cell, the transient change in membrane voltage results in the release of chemicals known as neuro-transmitters that can initiate an action potential in the other cell. This provides a means of rapid electrical communication between cells, analogous to passing a digital pulse from one cell to another.

If the action potential reaches a synapse with a muscle cell it can initiate an action potential that spreads over the surface of the muscle cell. This voltage change across the membrane of the muscle cell opens ion channels in the membrane that allow ions such as sodium, potassium and calcium to flow across the membrane, and can result in contraction of the muscle cell.

Increasing the voltage across the membrane of a cell below −70 millivolts is known as hyper-polarization and reduces the probability of an action potential being generated in the cell. This can be useful for reducing nerve activity and thereby reducing unwanted symptoms such as pain and spasticity The voltage across the membrane of a cell can be changed by creating an electric field in the tissues with a stimulator. It is important to note that action potentials are created within the mammalian nervous system by the brain, the sensory nervous system or other internal means. These action potentials travel along the body's nerve "highways". The TNSS creates an action potential through an externally applied electric field from outside the body. This is very different than how action potentials are naturally created within the body.

Electric Fields that can Cause Action Potentials

Referring to FIG. 2, electric fields capable of causing action potentials can be generated by electronic stimulators connected to electrodes that are implanted surgically in close proximity to the target nerves. To avoid the many issues associated with implanted devices, it is desirable to generate the required electric fields by electronic devices located on the surface of the skin. Such devices typically use square wave pulse trains of the form shown in FIG. 3. Such devices may be used instead of implants and/or with implants such as reflectors, conductors, refractors, or markers for tagging target nerves and the like, so as to shape electric fields to enhance nerve targeting and/or selectivity.

Figure 3:
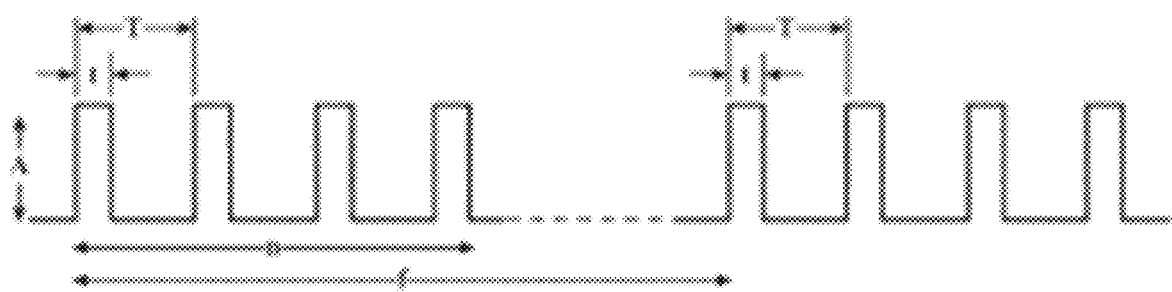
FIG. 3 is a graph showing pulses applied to the skin.
Figure 4:
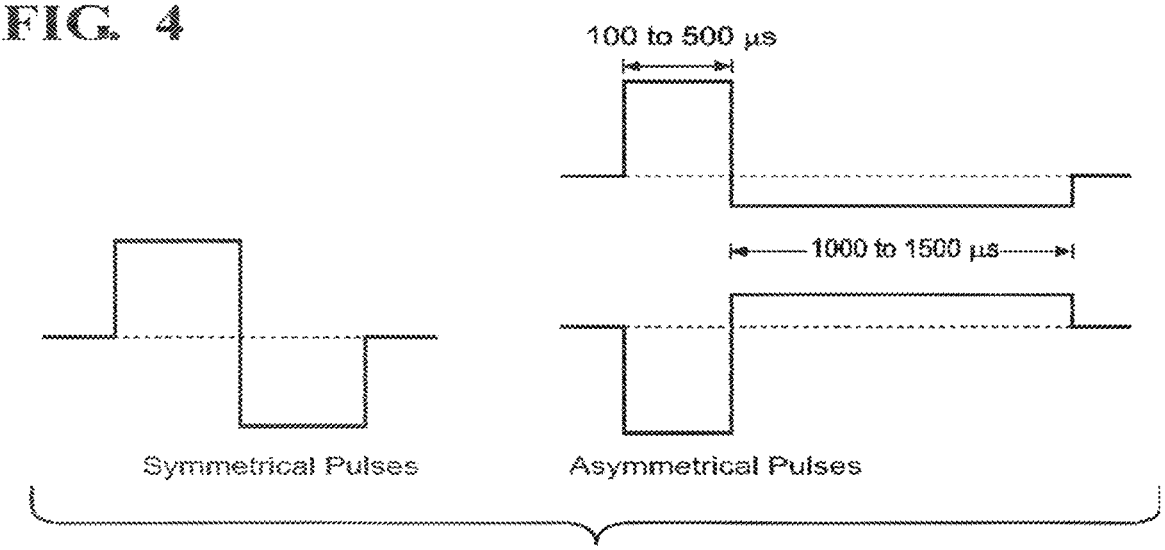
FIG. 4 is a graph showing symmetrical and asymmetrical pulses applied to the skin.

Referring to FIG. 3, the amplitude of the pulses "A", applied to the skin, may vary between 1 and 100 Volts, pulse width "t", between 100 microseconds and 10 milliseconds, duty cycle (t/T) between 0.1% and 50%, the frequency of the pulses within a group between 1 and 100/sec, and the number of pulses per group "n", between 1 and several hundred. Typically, pulses applied to the skin will have an amplitude of up to 60 volts, a pulse width of 250 microseconds and a frequency of 20 per second, resulting in a duty cycle of 0.5%. In some cases balanced-charge biphasic pulses will be used to avoid net current flow. Referring to FIG. 4, these pulses may be symmetrical, with the shape of the first part of the pulse similar to that of the second part of the pulse, or asymmetrical, in which the second part of the pulse has lower amplitude and a longer pulse width in order to avoid canceling the stimulatory effect of the first part of the pulse.

Formation of Electric Fields by Stimulators

The location and magnitude of the electric potential applied to the tissues by electrodes provides a method of shaping the electrical field. For example, applying two electrodes to the skin, one at a positive electrical potential with respect to the other, can produce a field in the underlying tissues such as that shown in the cross-sectional diagram of FIG. 5.

Figure 5:
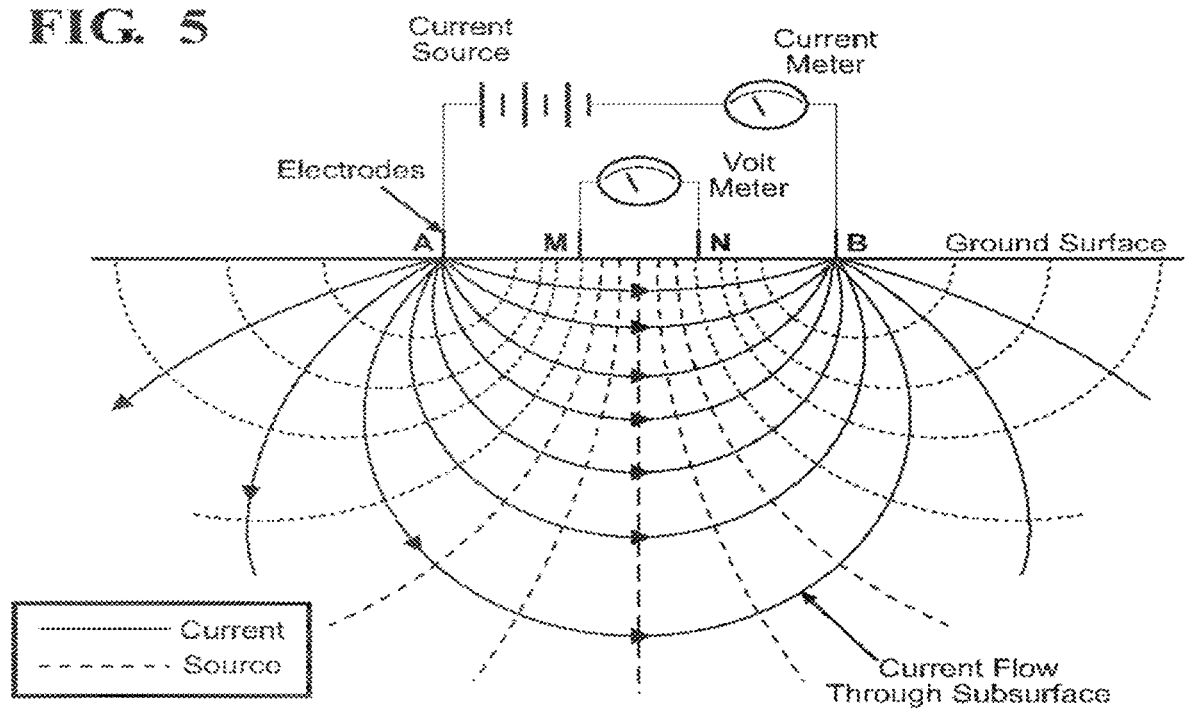
FIG. 5 is a cross-sectional diagram showing a field in underlying tissue produced by application of two electrodes to the skin.

The diagram in FIG. 5 assumes homogeneous tissue. The voltage gradient is highest close to the electrodes and lower at a distance from the electrodes. Nerves are more likely to be activated close to the electrodes than at a distance. For a given voltage gradient, nerves of large diameter are more likely to be activated than nerves of smaller diameter. Nerves whose long axis is aligned with the voltage gradient are more likely to be activated than nerves whose long axis is at right angles to the voltage gradient.

Figure 6:
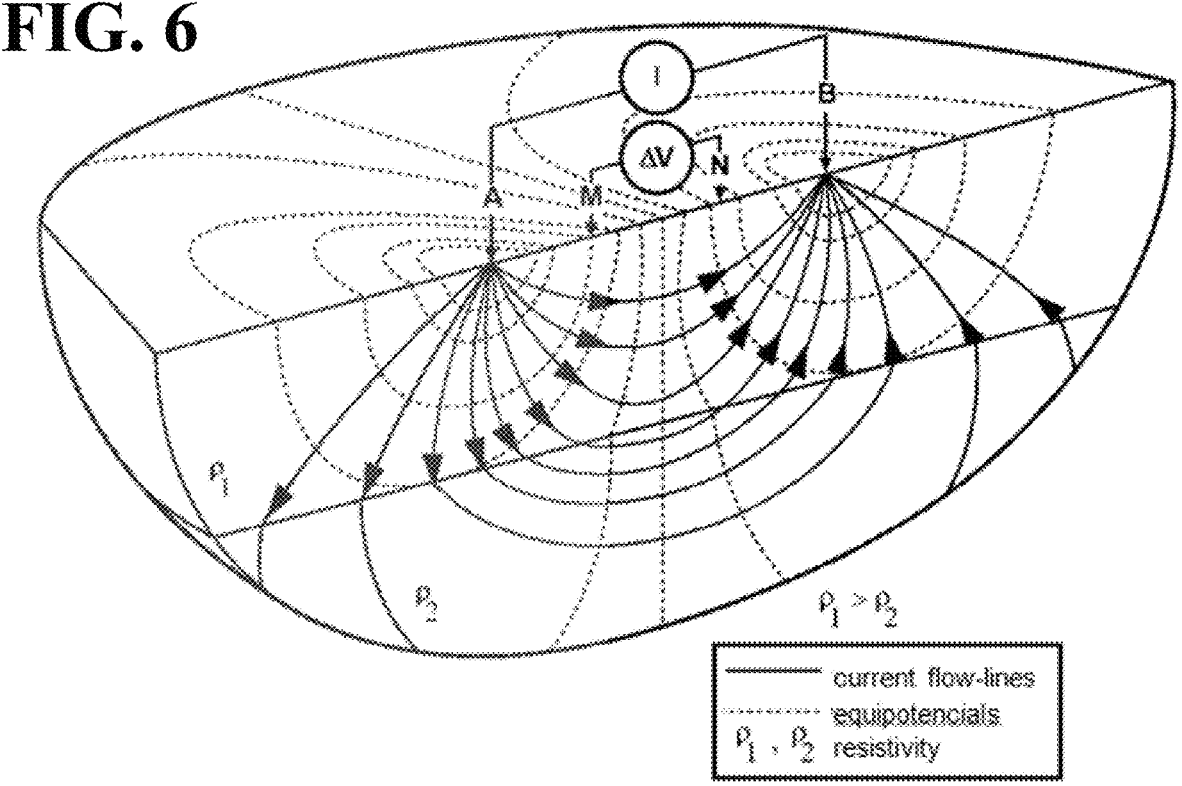
FIG. 6 is a cross-sectional diagram showing a field in underlying tissue produced by application of two electrodes to the skin, with two layers of tissue of different electrical resistivity.

Applying similar electrodes to a part of the body in which there are two layers of tissue of different electrical resistivity, such as fat and muscle, can produce a field such as that shown in FIG. 6. Layers of different tissue may act to refract and direct energy waves and be used for beam aiming and steering. An individual's tissue parameters may be measured and used to characterize the appropriate energy stimulation for a selected nerve.

Figure 7:
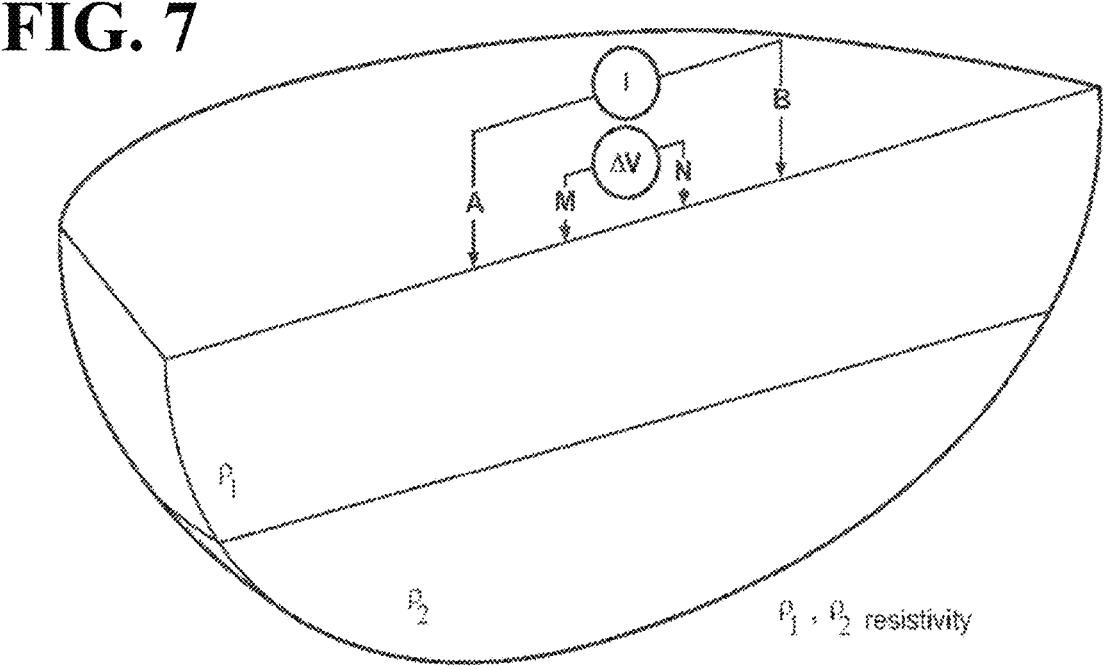
FIG. 7 is a cross-sectional diagram showing a field in underlying tissue when the stimulating pulse is turned off.

Referring to FIG. 7, when the stimulating pulse is turned off the electric field will collapse and the fields will be absent as shown. It is the change in electric field that will cause an action potential to be created in a nerve cell, provided sufficient voltage and the correct orientation of the electric field occurs. More complex three-dimensional arrangements of tissues with different electrical properties can result in more complex three-dimensional electric fields, particularly since tissues have different electrical properties and these properties are different along the length of a tissue and across it, as shown in Table 1.

TABLE 1

| Electrical Conductivity (siemens/m) | Direction | Average |
|---|---|---|
| Blood | | .65 |
| Bone | Along | .17 |
| Bone | Mixed | .095 |
| Fat | | .05 |
| Muscle | Along | .127 |
| Muscle | Across | .45 |

TABLE 1-continued

| Electrical Conductivity (siemens/m) | Direction | Average |
|---|---|---|
| Muscle | Mixed | .286 |
| Skin (Dry) | | .000125 |
| Skin (Wet) | | .00121 |

Modification of Electric Fields by Tissue

An important factor in the formation of electric fields used to create action potentials in nerve cells is the medium through which the electric fields must penetrate. For the human body this medium includes various types of tissue including bone, fat, muscle, and skin. Each of these tissues possesses different electrical resistivity or conductivity and different capacitance and these properties are anisotropic. They are not uniform in all directions within the tissues. For example, an axon has lower electrical resistivity along its axis than perpendicular to its axis. The wide range of conductivities is shown in Table 1. The three-dimensional structure and resistivity of the tissues will therefore affect the orientation and magnitude of the electric field at any given point in the body.

Modification of Electric Fields by Multiple Electrodes

Applying a larger number of electrodes to the skin can also produce more complex three-dimensional electrical fields that can be shaped by the location of the electrodes and the potential applied to each of them. Referring to FIG. 3, the pulse trains can differ from one another indicated by A, t/T, n, and f as well as have different phase relationships between the pulse trains. For example with an 8×8 array of electrodes, combinations of electrodes can be utilized ranging from simple dipoles, to quadripoles, to linear arrangements, to approximately circular configurations, to produce desired electric fields within tissues.

Applying multiple electrodes to a part of the body with complex tissue geometry will thus result in an electric field of a complex shape. The interaction of electrode arrangement and tissue geometry can be modeled using Finite Element Modeling, which is a mathematical method of dividing the tissues into many small elements in order to calculate the shape of a complex electric field. This can be used to design an electric field of a desired shape and orientation to a particular nerve.

High frequency techniques known for modifying an electric field, such as the relation between phases of a beam, cancelling and reinforcing by using phase shifts, may not apply to application of electric fields by TNSSs because they use low frequencies. Instead, examples use beam selection to move or shift or shape an electric field, also described as field steering or field shaping, by activating different electrodes, such as from an array of electrodes, to move the field. Selecting different combinations of electrodes from an array may result in beam or field steering. A particular combination of electrodes may shape a beam and/or change the direction of a beam by steering. This may shape the electric field to reach a target nerve selected for stimulation.

Activation of Nerves by Electric Fields

Typically, selectivity in activating nerves has required electrodes to be implanted surgically on or near nerves. Using electrodes on the surface of the skin to focus activation selectively on nerves deep in the tissues, as with examples of the invention, has many advantages. These include avoidance of surgery, avoidance of the cost of developing complex implants and gaining regulatory approval for them, and avoidance of the risks of long-term implants.

The features of the electric field that determine whether a nerve will be activated to produce an action potential can be modeled mathematically by the "Activating Function" disclosed in Rattay F., "The basic mechanism for the electrical stimulation of the nervous system", Neuroscience Vol. 89, No. 2, pp. 335-346 (1999). The electric field can produce a voltage, or extracellular potential, within the tissues that varies along the length of a nerve. If the voltage is proportional to distance along the nerve, the first order spatial derivative will be constant and the second order spatial derivative will be zero. If the voltage is not proportional to distance along the nerve, the first order spatial derivative will not be constant and the second order spatial derivative will not be zero. The Activating Function is proportional to the second-order spatial derivative of the extracellular potential along the nerve. If it is sufficiently greater than zero at a given point it predicts whether the electric field will produce an action potential in the nerve at that point. This prediction may be input to a nerve signature.

In practice, this means that electric fields that are varying sufficiently greatly in space or time can produce action potentials in nerves. These action potentials are also most likely to be produced where the orientation of the nerves to the fields change, either because the nerve or the field changes direction. The direction of the nerve can be determined from anatomical studies and imaging studies such as MRI scans. The direction of the field can be determined by the positions and configurations of electrodes and the voltages applied to them, together with the electrical properties of the tissues. As a result, it is possible to activate certain nerves at certain tissue locations selectively while not activating others.

To accurately control an organ or muscle, the nerve to be activated must be accurately selected. This selectivity may be improved by using examples disclosed herein as a nerve signature, in several ways, as follows:

(1) Improved algorithms to control the effects when a nerve is stimulated, for example, by measuring the resulting electrical or mechanical activity of muscles and feeding back this information to modify the stimulation and measuring the effects again. Repeated iterations of this process can result in optimizing the selectivity of the stimulation, either by classical closed loop control or by machine learning techniques such as pattern recognition and artificial intelligence;

(2) Improving nerve selectivity by labeling or tagging nerves chemically; for example, introduction of genes into some nerves to render them responsive to light or other electromagnetic radiation can result in the ability to activate these nerves and not others when light or electromagnetic radiation is applied from outside the body;

(3) Improving nerve selectivity by the use of electrical conductors to focus an electric field on a nerve; these conductors might be implanted, but could be passive and much simpler than the active implantable medical devices currently used;

(4) The use of reflectors or refractors, either outside or inside the body, is used to focus a beam of electromagnetic radiation on a nerve to improve nerve selectivity. If these reflectors or refractors are implanted, they may be passive and much simpler than the active implantable medical devices currently used;

(5) Improving nerve selectivity by the use of feedback from the person upon whom the stimulation is being performed; this may be an action taken by the person in response to a physical indication such as a muscle activation or a feeling from one or more nerve activations;

(6) Improving nerve selectivity by the use of feedback from sensors associated with the TNSS, or separately from other sensors, that monitor electrical activity associated with the stimulation; and (7) Improving nerve selectivity by the combination of feedback from both the person or sensors and the TNSS that may be used to create a unique profile of the user's nerve physiology for selected nerve stimulation.

Figure 8:
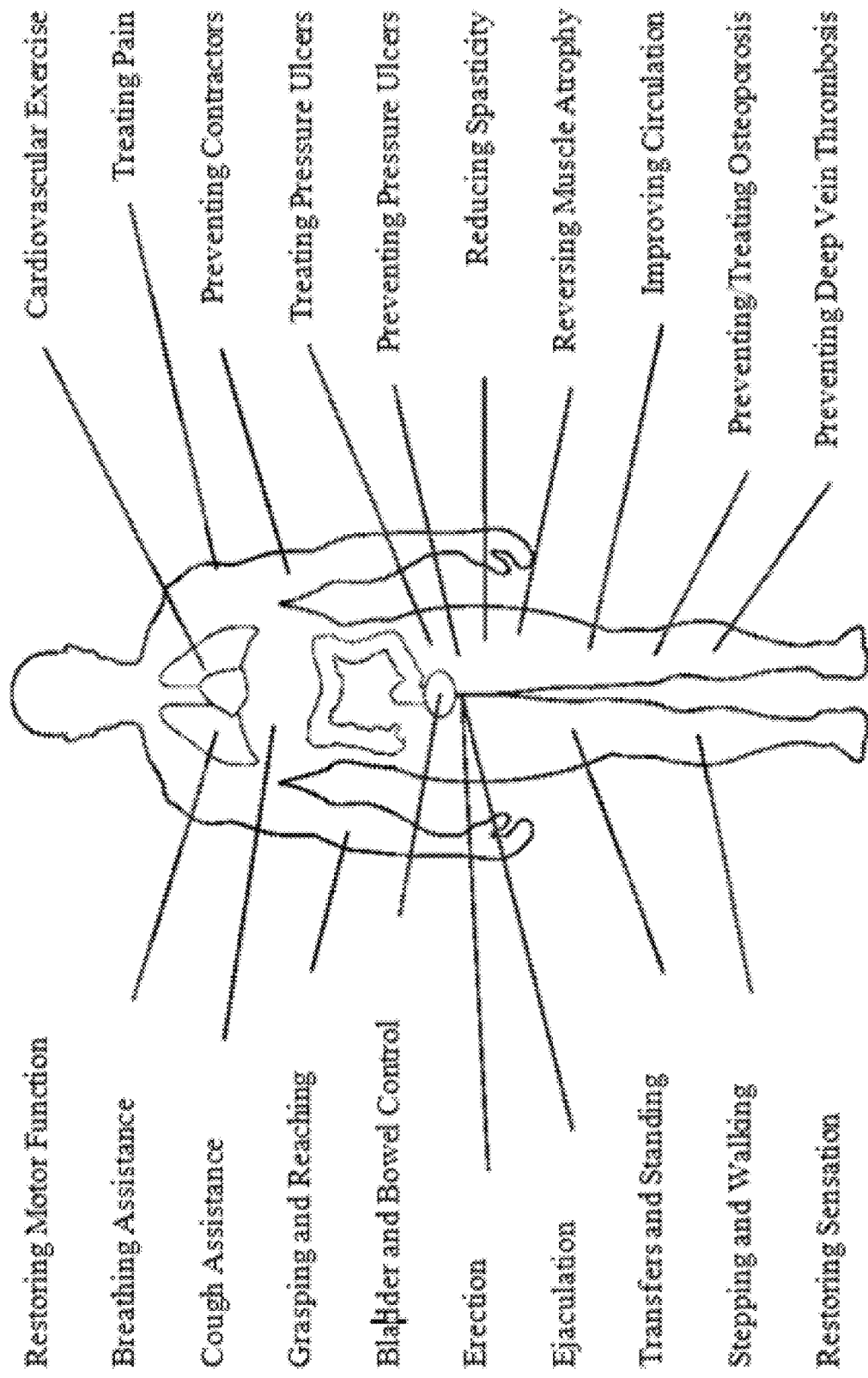
FIG. 8 shows potential applications of electrical stimulation to the body.

Potential applications of electrical stimulation to the body are shown in FIG. 8.

Figure 9A:
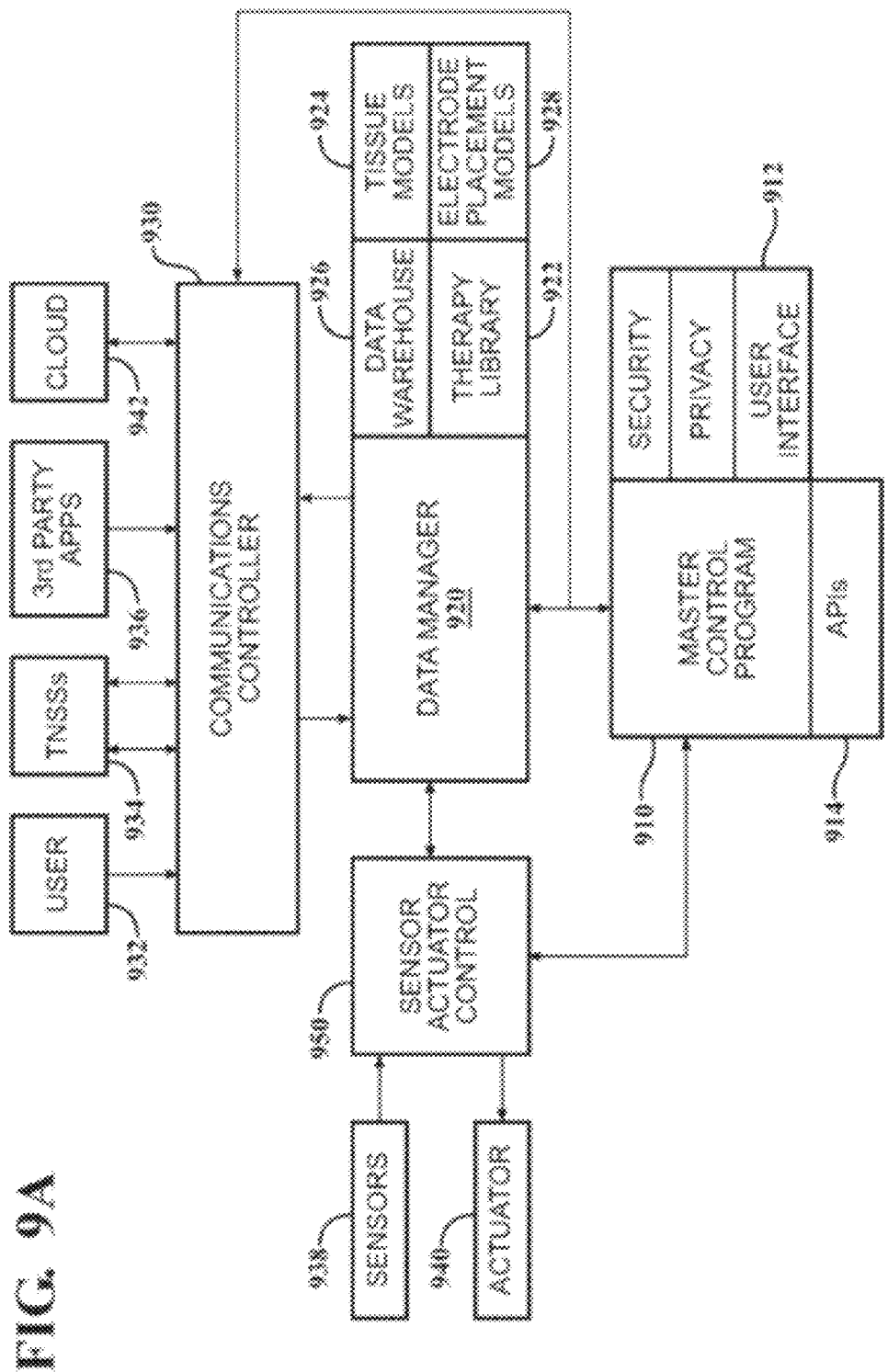
FIG. 9A is a system diagram of an example software and hardware components showing an example of a Topical Nerve Stimulator/Sensor (TNSS) interpreting a data stream from a control device in accordance with one example.

Referring to FIG. 9A, a TNSS 934 human and mammalian interface and its method of operation and supporting system are managed by a Master Control Program ("MCP") 910 represented in function format as block diagrams. It provides the logic for the nerve stimulator system in accordance to one example.

In one example, MCP 910 and other components shown in FIG. 9A are implemented by one or more processors that are executing instructions. The processor may be any type of general or specific purpose processor. Memory is included for storing information and instructions to be executed by the processor. The memory can be comprised of any combination of random access memory ("RAM"), read only memory ("ROM"), static storage such as a magnetic or optical disk, or any other type of computer readable media.

Master Control Program

The primary responsibility of MCP 910 is to coordinate the activities and communications among the various control programs, a Data Manager 920, a User 932, and the external ecosystem and to execute the appropriate response algorithms in each situation. The MCP 910 accomplishes electric field shaping and/or beam steering by providing an electrode activation pattern to TNSS device 934 to selectively stimulate a target nerve. For example, upon notification by a Communications Controller 930 of an external event or request, the MCP 910 is responsible for executing the appropriate response, and working with the Data Manager 920 to formulate the correct response and actions. It integrates data from various sources such as Sensors 938 and external inputs such as TNSS devices 934, and applies the correct security and privacy policies, such as encryption and HIPAA required protocols. It will also manage the User Interface (UI) 912 and the various Application Program Interfaces (APIs) 914 that provide access to external programs.

MCP 910 is also responsible for effectively managing power consumption by TNSS device 934 through a combination of software algorithms and hardware components that may include, among other things: computing, communications, and stimulating electronics, antenna, electrodes, sensors, and power sources in the form of conventional or printed batteries.

Communications Controller

Communications controller 930 is responsible for receiving inputs from the User 932, from a plurality of TNSS devices 934, and from 3rd party apps 936 via communications sources such as the Internet or cellular networks. The format of such inputs will vary by source and must be received, consolidated, possibly reformatted, and packaged for the Data Manager 920.

User inputs may include simple requests for activation of TNSS devices 934 to status and information concerning the User's 932 situation or needs. TNSS devices 934 will provide signaling data that may include voltage readings, TNSS 934 status data, responses to control program inquiries, and other signals. Communications Controller 930 is also responsible for sending data and control requests to the plurality of TNSS devices 934. 3rd party applications 936 can send data, requests, or instructions for the Master Control Program 910 or User 932 via the Internet or cellular networks. Communications Controller 930 is also responsible for communications via the cloud where various software applications may reside.

In one example, a user can control one or more TNSS devices using a remote fob or other type of remote device and a communication protocol such as Bluetooth. In one example, a mobile phone is also in communication and functions as a central device while the fob and TNSS device function as peripheral devices. In another example, the TNSS device functions as the central device and the fob is a peripheral device that communicates directly with the TNSS device (i.e., a mobile phone or other device is not needed).

Data Manager

The Data Manager (DM) 920 has primary responsibility for the storage and movement of data to and from the Communications Controller 930, Sensors 938, Actuators 940, and the Master Control Program 910. The DM 920 has the capability to analyze and correlate any of the data under its control. It provides logic to select and activate nerves. Examples of such operations upon the data include: statistical analysis and trend identification; machine learning algorithms; signature analysis and pattern recognition, correlations among the data within the Data Warehouse 926, the Therapy Library 922, the Tissue Models 924, and the Electrode Placement Models 928, and other operations. There are several components to the data that is under its control as disclosed below.

The Data Warehouse (DW) 926 is where incoming data is stored; examples of this data can be real-time measurements from TNSS devices 934 or from Sensors (938), data streams from the Internet, or control and instructional data from various sources. The DM 920 will analyze data, as described above, that is held in the DW 926 and cause actions, including the export of data, under MCP 910 control. Certain decision making processes implemented by the DM 920 will identify data patterns both in time, frequency, and spatial domains and store them as signatures for reference by other programs. Techniques such as EMG, or multi-electrode EMG, gather a large amount of data that is the sum of hundreds to thousands of individual motor units and the typical procedure is to perform complex decomposition analysis on the total signal to attempt to tease out individual motor units and their behavior. The DM 920 will perform big data analysis over the total signal and recognize patterns that relate to specific actions or even individual nerves or motor units. This analysis can be performed over data gathered in time from an individual, or over a population of TNSS Users.

The Therapy Library 922 contains various control regimens for the TNSS devices 934. Regimens specify the parameters and patterns of pulses to be applied by the TNSS devices 934. The width and amplitude of individual pulses may be specified to stimulate nerve axons of a particular size selectively without stimulating nerve axons of other sizes. The frequency of pulses applied may be specified to modulate some reflexes selectively without modulating other reflexes. There are preset regimens that may be loaded from the Cloud 942 or 3rd party apps 936. The regimens may be static read-only as well as adaptive with read-write capabilities so they can be modified in real-time responding to control signals or feedback signals or software updates. Referring to FIG. 3, one such example of a regimen has parameters A=40 volts, t=500 microseconds, T=1 Millisecond, n=100 pulses per group, and f=20 per second. Other examples of regimens will vary the parameters within ranges previously specified.

The Tissue Models 924 are specific to the electrical properties of particular body locations where TNSS devices 934 may be placed. As previously disclosed, electric fields for production of action potentials will be affected by the different electrical properties of the various tissues that they encounter. Tissue Models 924 are combined with regimens from the Therapy Library 922 and Electrode Placement Models 928 to produce desired actions. Tissue Models 924 may be developed by MRI, Ultrasound or other imaging or measurement of tissue of a body or particular part of a body. This may be accomplished for a particular User 932 and/or based upon a body norm. One such example of a desired action is the use of a Tissue Model 924 together with a particular Electrode Placement Model 928 to determine how to focus the electric field from electrodes on the surface of the body on a specific deep location corresponding to the pudendal nerve in order to stimulate that nerve selectively to reduce incontinence of urine. Other examples of desired actions may occur when a Tissue Model 924 in combination with regimens from the Therapy Library 22 and Electrode Placement Models 928 produce an electric field that stimulates a sacral nerve. Many other examples of desired actions follow for the stimulation of other nerves.

Electrode Placement Models 928 specify electrode configurations that the TNSS devices 934 may apply and activate in particular locations of the body. For example, a TNSS device 934 may have multiple electrodes and the Electrode Placement Model 928 specifies where these electrodes should be placed on the body and which of these electrodes should be active in order to stimulate a specific structure selectively without stimulating other structures, or to focus an electric field on a deep structure. An example of an electrode configuration is a 4 by 4 set of electrodes within a larger array of multiple electrodes, such as an 8 by 8 array. This 4 by 4 set of electrodes may be specified anywhere within the larger array such as the upper right corner of the 8 by 8 array. Other examples of electrode configurations may be circular electrodes that may even include concentric circular electrodes. The TNSS device 934 may contain a wide range of multiple electrodes of which the Electrode Placement Models 928 will specify which subset will be activated. The Electrode Placement Models 928 complement the regimens in the Therapy Library 922 and the Tissue Models 924 and are used together with these other data components to control the electric fields and their interactions with nerves, muscles, tissues and other organs. Other examples may include TNSS devices 934 having merely one or two electrodes, such as but not limited to those utilizing a closed circuit.

Sensor/Actuator Control

Independent sensors 938 and actuators 940 can be part of the TNSS system. Its functions can complement the electrical stimulation and electrical feedback that the TNSS devices 934 provide. An example of such a sensor 938 and actuator 940 include, but are not limited to, an ultrasonic actuator and an ultrasonic receiver that can provide real-time image data of nerves, muscles, bones, and other tissues. Other examples include electrical sensors that detect signals from stimulated tissues or muscles. The Sensor/Actuator Control module 950 provides the ability to control both the actuation and pickup of such signals, all under control of the MCP 910.

Application Program Interfaces

The MCP 910 is also responsible for supervising the various Application Program Interfaces (APIs) that will be made available for 3rd party developers. There may exist more than one API 914 depending upon the specific developer audience to be enabled. For example many statistical focused apps will desire access to the Data Warehouse 926 and its cumulative store of data recorded from TNSS 934 and User 932 inputs. Another group of healthcare professionals may desire access to the Therapy Library 922 and Tissue Models 924 to construct better regimens for addressing specific diseases or disabilities. In each case a different specific API 914 may be appropriate.

The MCP 910 is responsible for many software functions of the TNSS system including system maintenance, debugging and troubleshooting functions, resource and device management, data preparation, analysis, and communications to external devices or programs that exist on the smart phone or in the cloud, and other functions. However, one of its primary functions is to serve as a global request handler taking inputs from devices handled by the Communications Controller 930, external requests from the Sensor Control Actuator Module (950), and 3rd party requests 936. Examples of High Level Master Control Program (MCP) functions are disclosed below.

Figure 9B:
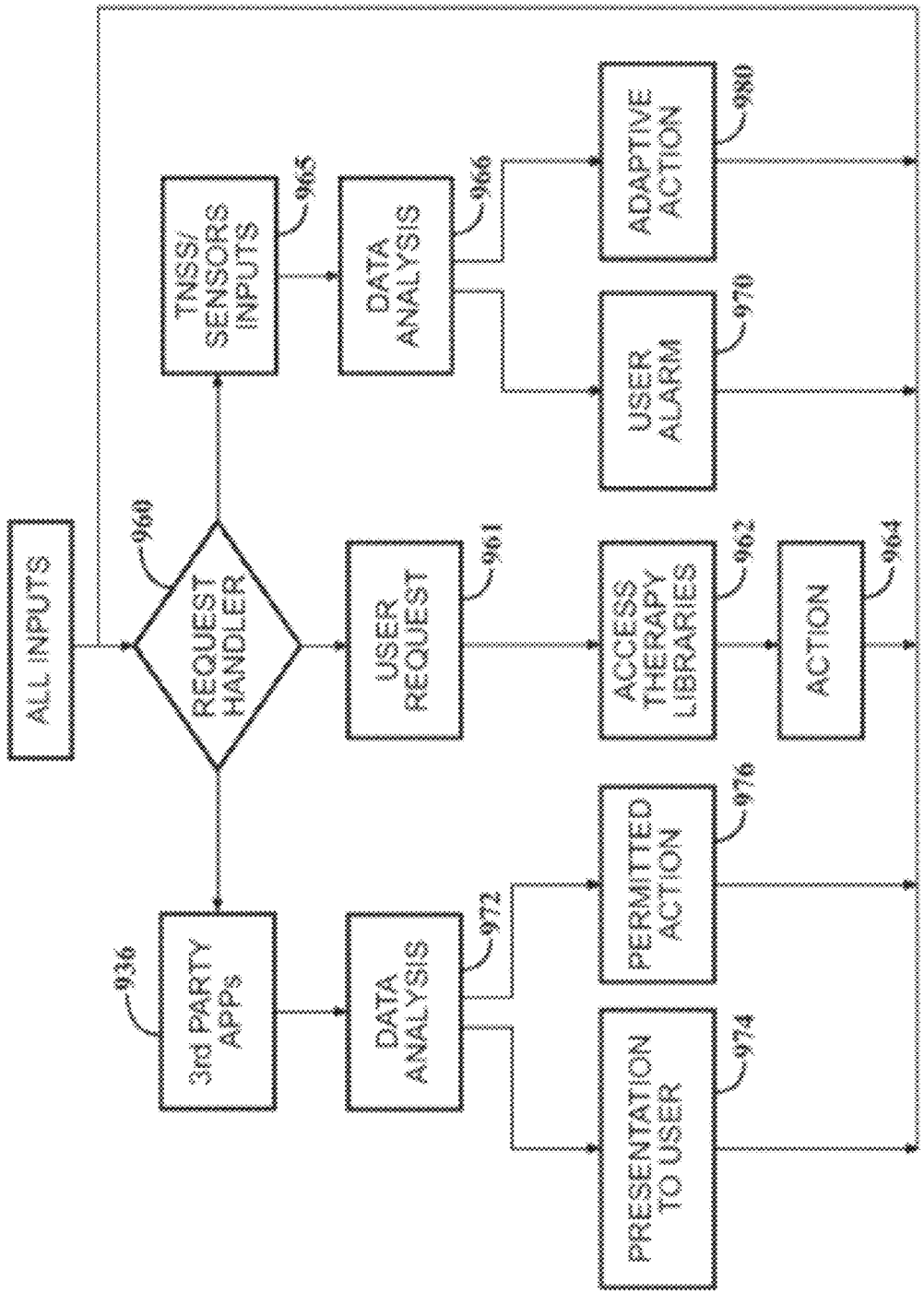
FIG. 9B is a flow chart showing an example of a function of a master control program in accordance with one example.

The manner in which the MCP handles these requests is shown in FIG. 9B. The Request Handler (RH) 960 accepts inputs from the User 932, TNSS devices 934, 3rd party apps 936, sensors 938 and other sources. It determines the type of request and dispatches the appropriate response as set forth in the following paragraphs.

User Request: The RH 960 will determine which of the plurality of User Requests 961 is present such as: activation; display status, deactivation, or data input, e.g. specific User condition. Shown in FIG. 9B is the RH's 960 response to an activation request. As shown in block 962, RH 960 will access the Therapy Library 922 and cause the appropriate regimen to be sent to the correct TNSS 934 for execution, as shown at block 964 labeled "Action."

TNSS/Sensor Inputs: The RH 960 will perform data analysis over TNSS 934 or Sensor inputs 965. As shown at block 966, it employs data analysis, which may include techniques ranging from DSP decision making processes, image processing algorithms, statistical analysis and other algorithms to analyze the inputs. In FIG. 9B two such analysis results are shown; conditions which cause a User Alarm 970 to be generated and conditions which create an Adaptive Action 980 such as causing a control feedback loop for specific TNSS 934 functions, which can iteratively generate further TNSS 934 or Sensor inputs 965 in a closed feedback loop.

3rd Party Apps: Applications can communicate with the MCP 910, both sending and receiving communications. A typical communication would be to send informational data or commands to a TNSS 934. The RH 960 will analyze the incoming application data, as shown at block 972. FIG. 9B shows two such actions that result. One action, shown at block 974 would be the presentation of the application data, possibly reformatted, to the User 932 through the MCP User Interface 912. Another result would be to perform a User 932 permitted action, as shown at 976, such as requesting a regimen from the Therapy Library 922.

Figure 10:
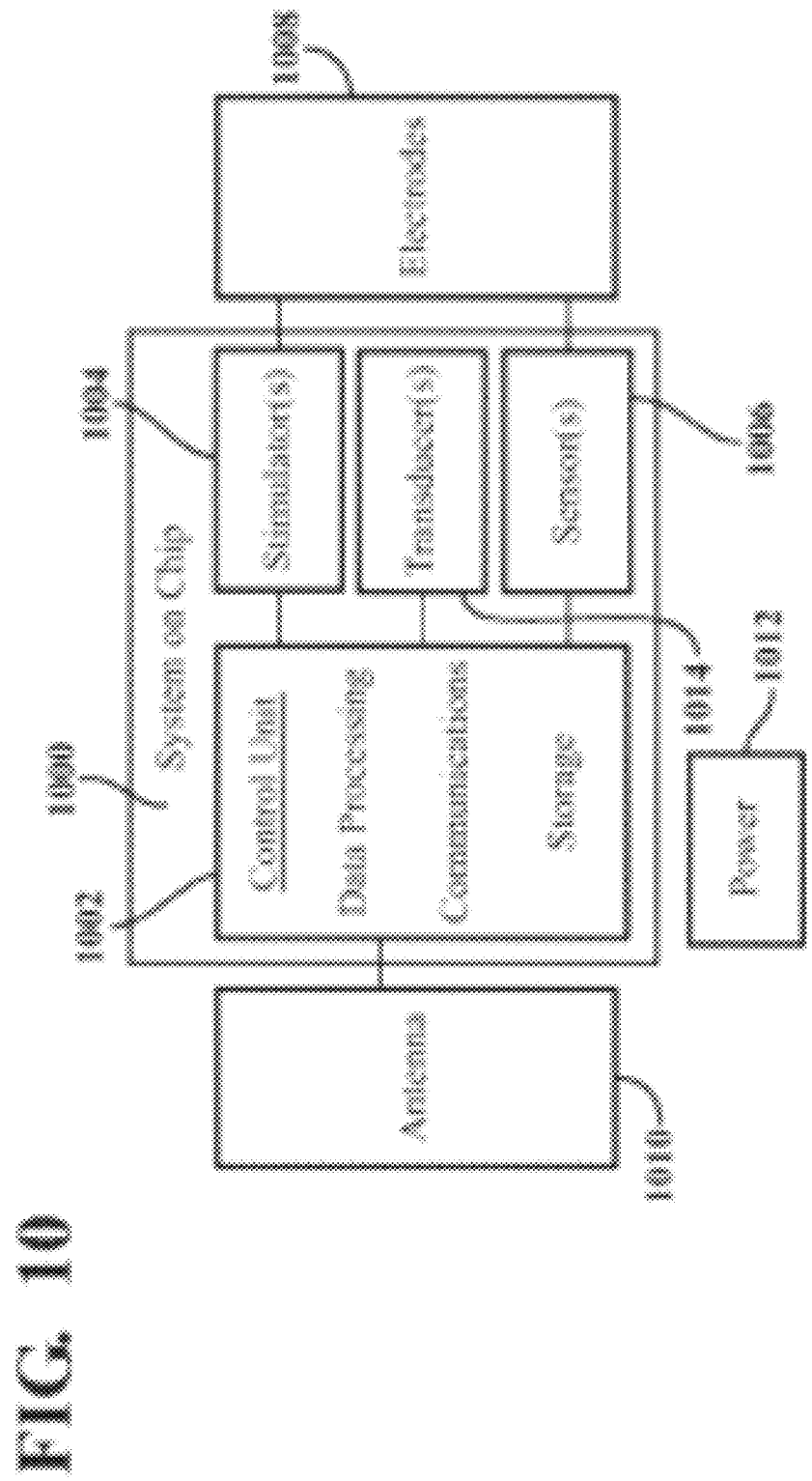
FIG. 10 is a block diagram of an example TNSS component configuration including a system on a chip (SOC) in accordance with one example.

Referring to FIG. 10, an example TNSS in accordance to one example is shown. The TNSS has one or more electronic circuits or chips 1000 that perform the functions of: communications with the controller, nerve stimulation via one or more electrodes 1008 that produce a wide range of electric field(s) according to treatment regimen, one or more antennae 1010 that may also serve as electrodes and communication pathways, and a wide range of sensors 1006 such as, but not limited to, mechanical motion and pressure, temperature, humidity, chemical and positioning sensors. In another example, TNSS interfaces to transducers 1014 to transmit signals to the tissue or to receive signals from the tissue.

One arrangement is to integrate a wide variety of these functions into an SOC, system on chip 1000. Within this is shown a control unit 1002 for data processing, communications, transducer interface and storage and one or more stimulators 1004 and sensors 1006 that are connected to electrodes 1008. An antenna 1010 is incorporated for external communications by the control unit. Also present is an internal power supply 1012, which may be, for example, a battery. An external power supply is another variation of the chip configuration. It may be necessary to include more than one chip to accommodate a wide range of voltages for data processing and stimulation. Electronic circuits and chips will communicate with each other via conductive tracks within the device capable of transferring data and/or power.

The TNSS interprets a data stream from the control device, such as that shown in FIG. 9A, to separate out message headers and delimiters from control instructions. In one example, control instructions contain information such as voltage level and pulse pattern. The TNSS activates the stimulator 1004 to generate a stimulation signal to the electrodes 1008 placed on the tissue according to the control instructions. In another example the TNSS activates a transducer 1014 to send a signal to the tissue. In another example, control instructions cause information such as voltage level and pulse pattern to be retrieved from a library stored in the TNSS.

The TNSS receives sensory signals from the tissue and translates them to a data stream that is recognized by the control device, such as the example in FIG. 9A. Sensory signals include electrical, mechanical, acoustic, optical and chemical signals among others. Sensory signals come to the TNSS through the electrodes 1008 or from other inputs originating from mechanical, acoustic, optical, or chemical transducers. For example, an electrical signal from the tissue is introduced to the TNSS through the electrodes 1008, is converted from an analog signal to a digital signal and then inserted into a data stream that is sent through the antenna 1010 to the control device. In another example an acoustic signal is received by a transducer 1014 in the TNSS, converted from an analog signal to a digital signal and then inserted into a data stream that is sent through the antenna 1010 to the control device. In certain examples sensory signals from the tissue are directly interfaced to the control device for processing.

An open loop protocol to control current to electrodes in known neural stimulation devices does not have feedback controls. It commands a voltage to be set, but does not check the actual Voltage. Voltage control is a safety feature. A stimulation pulse is sent based on preset parameters and cannot be modified based on feedback from the patient's anatomy. When the device is removed and repositioned, the electrode placement varies. Also the humidity and temperature of the anatomy changes throughout the day. All these factors affect the actual charge delivery if the voltage is preset.

In contrast, examples of the TNSS stimulation device have features that address these shortcomings using the Nordic Semiconductor nRF52832 microcontroller to regulate charge in a TNSS. The High Voltage Supply is implemented using a LED driver chip combined with a Computer controlled Digital Potentiometer to produce a variable voltage. A 3-1 step up Transformer then provides the desired High Voltage, "VBOOST", which is sampled to assure that no failure causes an incorrect Voltage level as follows. The nRF52832 Microcontroller samples the voltage of the stimulation waveform providing feedback and impedance calculations for an adaptive protocol to modify the waveform in real time. The Current delivered to the anatomy by the stimulation waveform is integrated using a differential integrator and sampled and then summed to determine actual charge delivered to the user for a Treatment. After every pulse in a Stimulation event, this measurement is analyzed and used to modify, in real time, subsequent pulses.

This hardware adaptation allows a firmware protocol to implement the adaptive protocol. This protocol regulates the charge applied to the body by changing VBOOST. A treatment is performed by a sequence of periodic pulses, which insert charge into the body through the electrodes. Some of the parameters of the treatment are fixed and some are user adjustable. The strength, duration and frequency may be user adjustable. The user may adjust these parameters as necessary for comfort and efficacy. The strength may be lowered if there is discomfort and raised if nothing is felt. The duration will be increased if the maximum acceptable strength results in an ineffective treatment.

Figure 11:
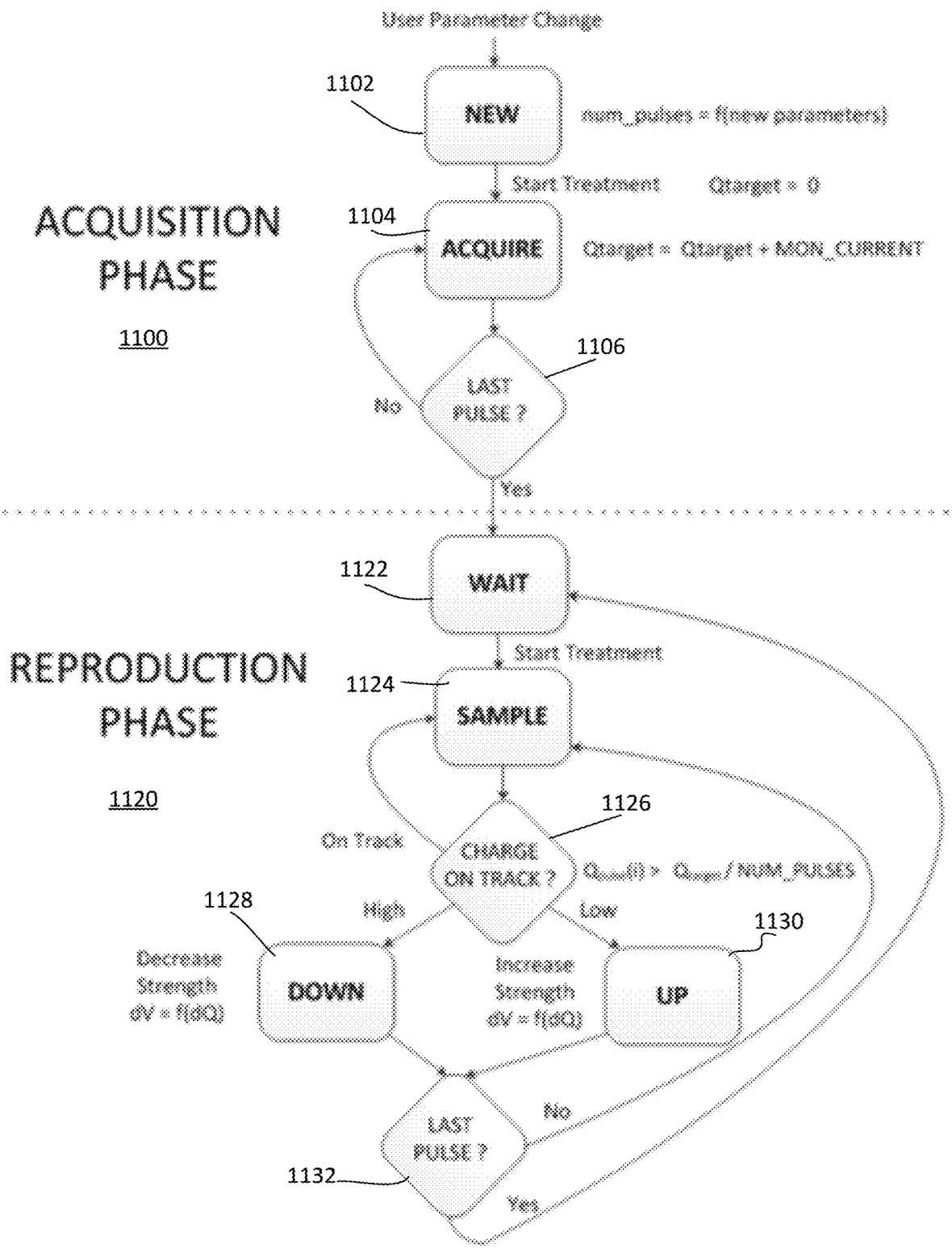
FIG. 11 is a flow diagram of the protocol for adaptive current control in accordance with one example.

A flow diagram in accordance with one example of the Adaptive Protocol disclosed above is shown in FIG. 11. The Adaptive Protocol strives to repeatedly and reliably deliver a target charge ("$Q_{target}$") during a treatment and to account for any environmental changes. Therefore, the functionality of FIG. 11 is to adjust the charge level applied to a user based on feedback, rather than use a constant level.

The mathematical expression of this protocol is as follows: $Q_{target} = Q_{target}(A*dS + B*dT)$, where A is the Strength Coefficient—determined empirically, dS is the user change in Strength, B is the Duration Coefficient—determined empirically, and dT is the user change in Duration.

Figure 12:
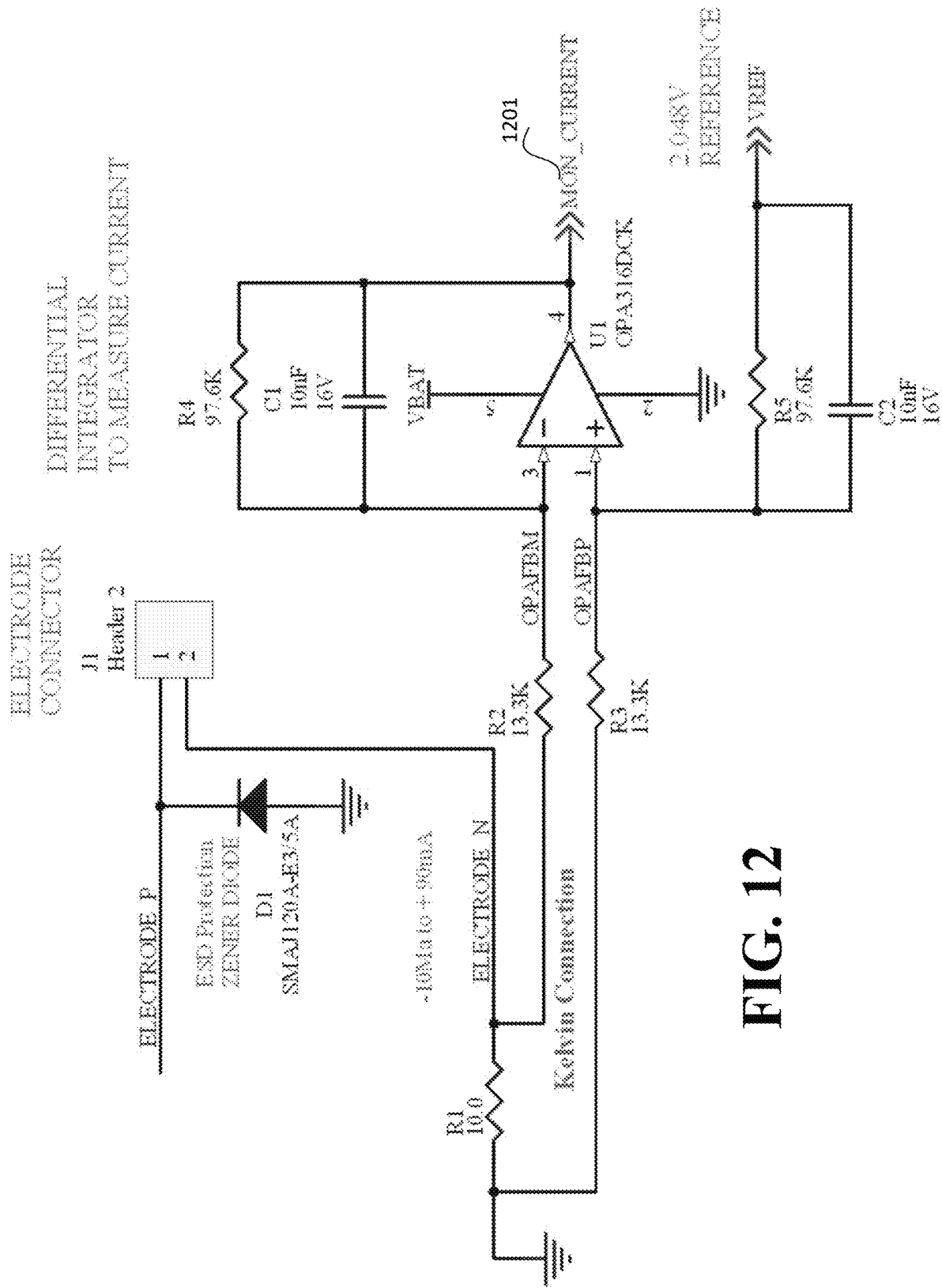
FIG. 12 is a Differential Integrator Circuit used in the Adaptive Current Protocol in accordance with one example.

The Adaptive Protocol includes two phases in one example: Acquisition 1100 and Reproduction 1120. Any change in user parameters places the Adaptive Protocol in the Acquisition phase. When the first treatment is started, a new baseline charge is computed based on the new parameters. At a new acquisition phase at 1102, all data from the previous charge application is discarded. In one example, 1102 indicates the first time for the current usage where the user places the TNSS device on a portion of the body and manually adjusts the charge level, which is a series of charge pulses, until it feels suitable, or any time the charge level is changed, either manually or automatically. The treatment then starts. The mathematical expression of this function of the application of a charge is as follows:
The charge delivered in a treatment is $$Q_{target} = \sum_{i=1}^{T*f} Q_{pulse}(i)$$

Where T is the duration; f is the frequency of "Rep Rate"; $Q_{pulse}(i)$ is the measured charge delivered by Pulse (i) in the treatment pulse train provided as a voltage MON_CURRENT that is the result of a Differential Integrator circuit shown in FIG. 12 (i.e., the average amount of charge per pulse). The Nordic microcontroller of FIG. 12 is an example of an Analog to Digital Conversion feature used to quantify voltage into a number representing the delivered charge and therefore determine the charge output. The number of pulses in the treatment is T*f.

At 1104 and 1106, every pulse is sampled. In one example, the functionality of 1104 and 1106 lasts for 10 seconds with a pulse rate of 20 Hz, which can be considered a full treatment cycle. The result of phase 1100 is the target pulse charge of $Q_{target}$.

Figure 13:
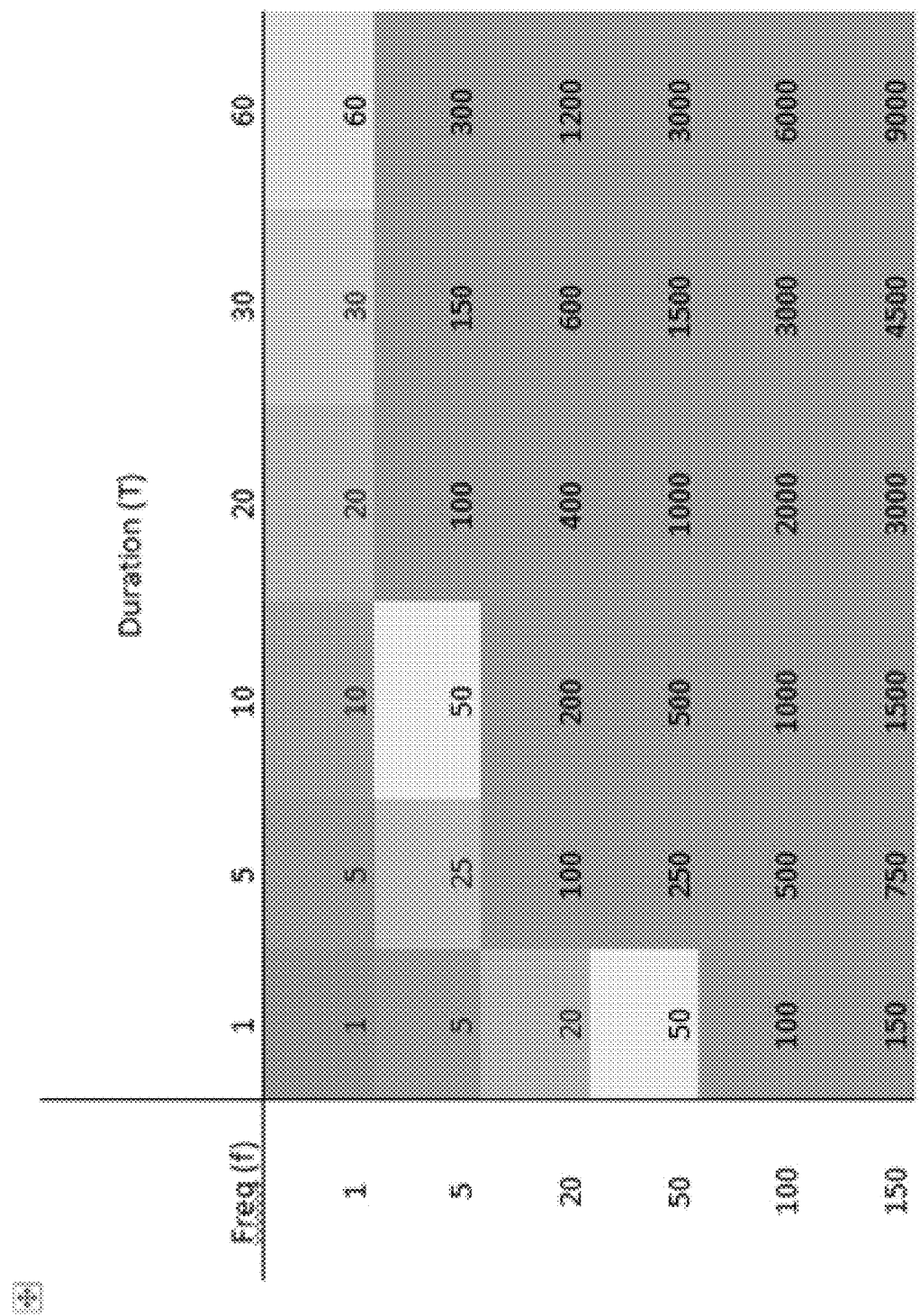
FIG. 13 is a table relating charge duration vs. frequency to provide feedback to the Adaptive Current Protocol in accordance with one example.

FIG. 13 is a table in accordance with one example showing the number of pulses per treatment measured against two parameters, frequency and duration. Frequency is shown on the Y-axis and duration on the X-axis. The Adaptive Current protocol in general performs better when using more pulses. One example uses a minimum of 100 pulses to provide for solid convergence of charge data feedback. Referring to the FIG. 13, a frequency setting of 20 Hz and duration of 10 seconds produces 200 pulses, which is desirable to allow the Adaptive Current Protocol to reproduce a previous charge.

The reproduction phase 1120 begins in one example when the user initiates another subsequent treatment after acquisition phase 1100 and the resulting acquisition of the baseline charge, $Q_{target}$. For example, a full treatment cycle, as discussed above, may take 10 seconds. After, for example, a two-hour pause as shown at wait period 1122, the user may then initiate another treatment. During this phase, the Adaptive Current Protocol attempts to deliver $Q_{target}$ for each subsequent treatment. The functionality of phase 1120 is needed because, during the wait period 1122, conditions such as the impedance of the user's body due to sweat or air humidity may have changed. The differential integrator is sampled at the end of each Pulse in the Treatment. At that point, the next treatment is started and the differential integrator is sampled for each pulse at 1124 for purposes of comparison to the acquisition phase $Q_{target}$. Sampling the pulse includes measuring the output of the pulse in coulombs. The output of the integrator of FIG. 12 in voltage, referred to as Mon_Current 1201, is a direct linear relationship to the delivered charge in micro-coulombs and provides a reading of how much charge is leaving the device and entering the user. At 1126, each single pulse is compared to the charge value determined in phase 1100 (i.e., the target charge) and the next pulse will be adjusted in the direction of the difference.

$$NUM\_PULSES = (T*f)$$

After each pulse, the observed charge, $Q_{pulse}(i)$, is compared to the expected charge per pulse.

$$Q_{pulse}(i) > Q_{target}/NUM\_PULSES?$$

The output charge or "VBOOST" is then modified at either 1128 (decreasing) or 1130 (increasing) for the subsequent pulse by:

$$dV(i) = G[Q_{target}/NUM\_PULSES - Q_{pulse}(i)]$$

where G is the Voltage adjustment Coefficient—determined empirically. The process continues until the last pulse at 1132.

A safety feature assures that the VBOOST will never be adjusted higher by more than 10%. If more charge is necessary, then the repetition rate or duration can be increased.

In one example, in general, the current is sampled for every pulse during acquisition phase 1100 to establish target charge for reproduction. The voltage is then adjusted via a digital potentiometer, herein referred to as "Pot", during reproduction phase 1120 to achieve the established target_charge.

The digital Pot is calibrated with the actual voltage at startup. A table is generated with sampled voltage for each wiper value. Tables are also precomputed storing the Pot wiper increment needed for 1 v and 5 v output delta at each pot level. This enables quick reference for voltage adjustments during the reproduction phase. The tables may need periodic recalibration due to battery level.

In one example, during acquisition phase 1100, the minimum data set=100 pulses and every pulse is sampled and the average is used as the target_charge for reproduction phase 1120. In general, less than 100 pulses may provide an insufficient data sample to use as a basis for reproduction phase 1120. In one example, the default treatment is 200 pulses (i.e., 20 Hz for 10 seconds). In one example, a user can adjust both duration and frequency manually.

In one example, during acquisition phase 1100, the maximum data set=1000 pulses. The maximum is used to avoid overflow of 32 bit integers in accumulating the sum of samples. Further, 1000 pulses in one example is a sufficiently large data set and collecting more is likely unnecessary.

After 1000 pulses for the above example, the target_charge is computed. Additional pulses beyond 1000 in the acquisition phase do not contribute to the computation of the target charge.

In one example, the first 3-4 pulses are generally higher than the rest so these are not used in acquisition phase 1100. This is also accounted for in reproduction phase 1120. Using these too high values can result in target charge being set too high and over stimulating on the subsequent treatments in reproduction phase 1120. In other examples, more advanced averaging algorithms could be applied to eliminating high and low values.

In an example, there may be a safety concern about automatically increasing the voltage. For example, if there is poor connection between the device and the user's skin, the voltage may auto-adjust at 1130 up to the max. The impedance may then be reduced, for example by the user pressing the device firmly, which may result in a sudden high current. Therefore, in one example, if the sample is 500 mv or more higher than the target, it immediately adjusts to the minimum voltage. This example then remains in reproduction phase 1120 and should adjust back to the target current/charge level. In another example, the maximum voltage increase is set for a single treatment (e.g., 10V). More than that should not be needed in normal situations to achieve the established target_charge. In another example, a max is set for VBOOST (e.g., 80V).

In various examples, it is desired to have stability during reproduction phase 1120. In one example, this is accomplished by adjusting the voltage by steps. However, a relatively large step adjustment can result in oscillation or over stimulation. Therefore, voltage adjustments may be made in smaller steps. The step size may be based on both the delta between the target and sample current as well as on the actual VBOOST voltage level. This facilitates a quick and stable/smooth convergence to the target charge and uses a more gradual adjustments at lower voltages for more sensitive users.

The following are the conditions that may be evaluated to determine the adjustment step.

delta-mon_current=abs(sample_mon_current−target_charge)

If delta_mon_current>500 mv and VBOOST>20V then step=5V for increase adjustments (For decrease adjustments a 500 mv delta triggers emergency decrease to minimum Voltage)

If delta_mon_current>200 mv then step=1V

If delta_mon_current>100 mv and delta_mon_current>5%*sample_mon_current then step=1V In other examples, new treatments are started with voltage lower than target voltage with a voltage buffer of approximately 10%. The impedance is unknown at the treatment start. These examples save the target_voltage in use at the end of a treatment. If the user has not adjusted the strength parameter manually, it starts a new treatment with saved target_voltage with the 10% buffer. This achieves target current quickly with the 10% buffer to avoid possible over stimulation in case impedance has been reduced. This also compensates for the first 3-4 pulses that are generally higher.

As disclosed, examples apply an initial charge level, and then automatically adjust based on feedback of the amount of current being applied. The charge amount can be varied up or down while being applied. Therefore, rather than setting and then applying a fixed voltage level throughout a treatment cycle, implementations of the invention measure the amount of charge that is being input to the user, and adjust accordingly throughout the treatment to maintain a target charge level that is suitable for the current environment.

Several examples are specifically illustrated and/or described herein. However, it will be appreciated that modifications and variations of the disclosed examples are covered by the above teachings and within the purview of the appended claims without departing from the spirit and intended scope of the invention.

What is claimed is:

1. A method of providing a nerve stimulation treatment using electrodes coupled to a user, the method comprising:
    affixing a patch externally on a dermis of the user, the patch comprising a flexible substrate and an adhesive on a first side adapted to adhere to the dermis of the user, and electronic components directly coupled to the substrate, the electronic components comprising a processor, circuitry for measuring a charge value of an electrical pulse applied to the dermis, and the electrodes;
    determining a target charge level;
    outputting a series of the electrical pulses from the electrodes;
    for one or more of each pulse outputted, the processor using the circuitry to determine a charge value of the pulse and comparing the charge value to the target charge level;
    if the charge value is greater than the target charge level, reducing a strength level of a subsequent outputted pulse; and
    if the charge value is less than the target charge level, increasing the strength level of a subsequent outputted pulse.

2. The method of claim 1, in which the series of pulses are defined based on a frequency and a duration.

3. The method of claim 1, in which determining the target charge level $Q_{target}$ comprises generating an acquisition series of pulses and $$Q_{target} = \sum_{i=1}^{T*f} Q_{pulse}(i),$$

where T is a duration of the acquisition series of pulses, f is a frequency of the acquisition series of pulses and $Q_{pulse}(i)$ is a measured charge of each of the acquisition series of pulses.

4. The method of claim 1, in which the measuring the charge value of the pulse comprises determining an output of a differential integrator.

5. The method of claim 1, in which the series of pulses comprises at least 100 pulses.

6. The method of claim 1, in which an amount of the reducing the strength and increasing the strength is limited by a predefined step value.

7. The method of claim 1, in which the determining the target charge level occurs after a manual adjustment of a voltage output level.

8. A nerve stimulation device comprising:
    a flexible substrate having an adhesive on a first side adapted to adhere to a dermis of a user, and electronic components directly coupled to the substrate, the electronic components comprising:
    electrodes;
    circuitry for measuring a charge value of an electrical pulse applied to the dermis; and
    a processor coupled to the electrodes and the circuitry, the processor executing instructions to implement nerve stimulation comprising:
    determining a target charge level;
    outputting a series of pulses from the electrodes;
    for one or more of each pulse outputted, using the circuitry to determine a charge value of the pulse and compare the charge value to the target charge level;
    if the charge value is greater than the target charge level, reducing a strength level of a subsequent outputted pulse; and
    if the charge value is less than the target charge level, increasing the strength level of a subsequent outputted pulse.

9. The nerve stimulation device of claim 8, in which the series of pulses are defined based on a frequency and a duration.

10. The nerve stimulation device of claim 8, in which determining the target charge level $Q_{target}$ comprises generating an acquisition series of pulses and $$Q_{target} = \sum_{i=1}^{T*f} Q_{pulse}(i),$$

where T is a duration of the acquisition series of pulses, f is a frequency of the acquisition series of pulses and $Q_{pulse}(i)$ is a measured charge of each of the acquisition series of pulses.

11. The nerve stimulation device of claim 8, in which the measuring the charge value of the pulse comprises determining an output of a differential integrator.

12. The nerve stimulation device of claim 8, in which the series of pulses comprises at least 100 pulses.

13. The nerve stimulation device of claim 8, in which an amount of the reducing the strength and increasing the strength is limited by a predefined step value.

14. The nerve stimulation device of claim 8, in which the determining the target charge level occurs after a manual adjustment of a voltage output level.

15. A non-transitory computer-readable medium having instructions stored thereon that, when executed by a processor, cause the processor to provide a nerve stimulation treatment using electrodes coupled to a user by affixing a patch externally on a dermis of the user, the patch comprising a flexible substrate and an adhesive on a first side adapted to adhere to the dermis of the user, and electronic components directly coupled to the substrate, the electronic components comprising a processor, circuitry for measuring a charge value of an electrical pulse applied to the dermis, and the electrodes, the nerve stimulation treatment comprising:
  determining a target charge level;
  outputting a series of the electrical pulses from the electrodes;
  for one or more of each pulse outputted, the processor using the circuitry to determine a charge value of the pulse and comparing the charge value to the target charge level;
  if the charge value is greater than the target charge level, reducing a strength level of a subsequent outputted pulse; and
  if the charge value is less than the target charge level, increasing the strength level of a subsequent outputted pulse.

16. The non-transitory computer-readable medium of claim 15, in which the series of pulses are defined based on a frequency and a duration.

17. The non-transitory computer-readable medium of claim 15, in which determining the target charge level $Q_{target}$ comprises generating an acquisition series of pulses and $$Q_{target} = \sum_{i=1}^{T*f} Q_{pulse}(i),$$

where T is a duration of the acquisition series of pulses, f is a frequency of the acquisition series of pulses and $Q_{pulse}(i)$ is a measured charge of each of the acquisition series of pulses.

18. The non-transitory computer-readable medium of claim 15, in which the measuring the charge value of the pulse comprises determining an output of a differential integrator.

19. The non-transitory computer-readable medium of claim 15, in which the series of pulses comprises at least 100 pulses.

20. The non-transitory computer-readable medium of claim 15, in which an amount of the reducing the strength and increasing the strength is limited by a predefined step value.

21. The non-transitory computer-readable medium of claim 15, in which the determining the target charge level occurs after a manual adjustment of a voltage output level.

* * * * *